(12) United States Patent
Garcia Armenta

(10) Patent No.: US 12,290,526 B2
(45) Date of Patent: May 6, 2025

(54) SYNERGISTIC PHARMACEUTICAL COMPOSITION COMPRISING ACECLOFENAC AND BETAMETHASONE FOR THE TREATMENT OF PAIN IN LOCALISED FORMS OF RHEUMATIC ILLNESSES

(71) Applicants: Federico Amezcua Amezcua, Jalisco (MX); Carlos Amezcua Amezcua, Jalisco (MX)

(72) Inventor: Patricia Del Carmen Garcia Armenta, Jalisco (MX)

(73) Assignees: Federico Amezcua Amezcua, Jalisco (MX); Carlos Amezcua Amezcua, Jalisco (MX)

( * ) Notice: Subject to any disclaimer, the term of this patent is extended or adjusted under 35 U.S.C. 154(b) by 338 days.

(21) Appl. No.: 17/267,239

(22) PCT Filed: Aug. 13, 2019

(86) PCT No.: PCT/MX2019/000091
§ 371 (c)(1),
(2) Date: Feb. 9, 2021

(87) PCT Pub. No.: WO2020/036478
PCT Pub. Date: Feb. 20, 2020

(65) Prior Publication Data
US 2021/0228598 A1    Jul. 29, 2021

(30) Foreign Application Priority Data
Aug. 13, 2018  (MX) .......................... A/2018/009812

(51) Int. Cl.
*A61K 31/573*    (2006.01)
*A61K 9/00*      (2006.01)
*A61K 31/216*    (2006.01)
*A61P 29/00*     (2006.01)

(52) U.S. Cl.
CPC .......... *A61K 31/573* (2013.01); *A61K 9/0014* (2013.01); *A61K 9/0019* (2013.01); *A61K 31/216* (2013.01); *A61P 29/00* (2018.01)

(58) Field of Classification Search
CPC .............. A61K 2300/00; A61K 31/196; A61K 31/216; A61K 31/573; A61K 31/661; A61K 45/06; A61K 9/0014; A61K 9/0019; A61P 19/02; A61P 29/00
See application file for complete search history.

(56) References Cited

U.S. PATENT DOCUMENTS

| 6,423,697 B1 | 7/2002 | Friedman |
| 8,802,136 B2 * | 8/2014 | Miller, II .............. A61K 9/7084 424/443 |
| 2016/0243040 A1 * | 8/2016 | Amezcua Amezcua ..................... A61K 9/2095 |

FOREIGN PATENT DOCUMENTS

| CN | 102302779 A * | 1/2012 | .......... A61K 31/565 |
| RU | 2017123271 A | 1/2019 | |
| RU | 2017123274 A | 1/2019 | |
| WO | 2007037666 A1 | 4/2007 | |
| WO | 2007072503 A2 | 6/2007 | |
| WO | WO-2007099559 A2 * | 9/2007 | .......... A61K 31/216 |
| WO | 2015016698 A1 | 2/2015 | |

OTHER PUBLICATIONS

Karmoker, The Pharma Innovation Journal 2016; 5(3): 03-07 (Year: 2016).*
Kopylov, Journal of Pharmaceutical and Biomedical Analysis, vol. 149, Feb. 5, 2018, pp. 278-289 (Year: 2018).*
International Search Report ISA/ES in PCT/MX2019/000091, dated Feb. 10, 2020; 4pgs.

* cited by examiner

*Primary Examiner* — Jean P Cornet
(74) *Attorney, Agent, or Firm* — Haukaas Fortius PLLC; Michael Haukaas; Paul K. Judd

(57) ABSTRACT

This invention is related to a pharmaceutical composition made up by the synergic combination of a nonsteroidal anti-inflammatory analgesic such as Aceclofenac or its pharmaceutically acceptable salts and an anti-inflammatory steroid agent such as the active ingredient Betamethasone or its pharmaceutically acceptable phosphate or dipropionate salts, which are formulated in a single dosing unit for topical, intramuscular or intravenous administration, which is indicated for the treatment of the localized pain of rheumatic diseases.

2 Claims, 1 Drawing Sheet

SYNERGISTIC PHARMACEUTICAL COMPOSITION COMPRISING ACECLOFENAC AND BETAMETHASONE FOR THE TREATMENT OF PAIN IN LOCALISED FORMS OF RHEUMATIC ILLNESSES

CROSS-REFERENCE TO RELATED APPLICATIONS

This application is a National Stage filing under 35 U.S.C. § 371 of International Application No. PCT/MX2019/000091, filed Aug. 13, 2019, which claims the benefit of Mexican Patent Application No. MX/a/2018/009812 filed Aug. 13, 2018, which applications are incorporated herein by reference.

FIELD OF INVENTION

This invention is connected with the technical field of the pharmaceutical industry, as its purpose is to provide a pharmaceutical composition that consists of the synergistic drug combination of a nonsteroidal anti-inflammatory agent (NSAID), made up by the active ingredient aceclofenac or its pharmaceutically acceptable salts and an anti-inflammatory steroid agent from the group of corticosteroids such as the active ingredient betamethasone or a chosen pharmaceutically acceptable salt thereof of phosphate or dipropionate, as well as pharmaceutically acceptable vehicles, excipients or adjuvants, formulated in semi-solid or solution as aerosol for topical application. Said combination is indicated for the control and treatment of pain in the localized forms of rheumatic conditions.

The combination of the aforementioned active ingredients produces a stronger therapeutic effect when they are applied together in a single dosage unit, unlike when they are administered separately, providing the benefits of a smaller dose being required, higher therapeutic effect and fewer adverse effects.

BACKGROUND

At the present time there are a lot of health problems with a magnitude or significance that is hugely relevant for Public Health. In this regard, there is a set of diseases that has damage to the musculoskeletal system in common and that health professionals seldom mention, as in most cases they tend to think that these are diseases that hardly have any effect on our daily lives or that they are exclusively a problem of old age.

Conditions of the musculoskeletal system are generally referred to as rheumatic diseases and are more common than is often assumed. As regards to the demand for services in Mexico, rheumatic diseases represent the third most important reason for visits to GPs (16%). Rheumatic diseases were the first cause of permanent disability through general disease, in accordance with the facts already given and according to data from the INEGI (National Institute of Statistics, Geography and Informatics) for the 1995 population of approximately 93 million. There must be between 270,000 and 900,000 patients with rheumatoid arthritis and around 6,000,0000 people with degenerative joint disease (Rheumatology) in our country. That being said, rheumatic diseases have a serious impact that can become much more serious if other common health problems such as obesity, which has acquired epidemic levels Mexico, are added to the mix.

Rheumatic diseases are among the main causes of disability. They vary in seriousness from slight pains in joints and the associated structures (such as muscles, tendons, ligaments) to serious abnormalities that can endanger patients' lives. Therefore, rheumatology covers a wide range of diseases, some of which are listed below: Rheumatoid arthritis; Osteoarthritis; Ankylosing spondylitis; Bursitis; Tendinitis; Synovitis; Pain in the lumbar region (lumbago); Crystal arthropathies (such as gout); Psoriatic arthritis.

RA (rheumatoid arthritis) is a systemic, chronic, inflammatory, autoimmune disease that affects connective tissue and involves several joints. It is a highly disabling progressive pathology and predominates in female patients.

It is estimated that 10% of the world's population develops a rheumatic disease during their lifetime. According to the World Health Organization's 1998 report on world health, approximately 190 million people suffer from degenerative joint diseases and 16.5 million have rheumatoid arthritis. The worldwide prevalence of rheumatoid arthritis is considered to be 1% (0.3-2.1%). While 15% of men and 25% of women older than 60 years of age have symptomatic degenerative joint disease.

The most frequent clinical symptoms are: arthralgia, morning stiffness, fatigue, weight loss and slight fever. There may be a clinic of carpal tunnel syndrome. It can start in the feet and the metatarsophalangeal joints.

Osteoarthritis, the most common form of arthritis, is a chronic and degenerative disease of the joints that mainly affects middle-aged and old adults.

Osteoarthritis is characterized by the disintegration of the cartilage in the joints and the adjacent bone in the neck, the lower back, knees and/or fingers.

This arthropathy is characterized by the degeneration of the cartilage and bone hypertrophy on articular edges, the inflammation is generally minimum.

Osteoarthritis has been mainly divided into 2 types:
PRIMARY: Which mainly affects some or all the distal interphalangeal joints (Heberden nodes) and, less frequently, the proximal interphalangeal joints (Bouchard nodes), the metacarpophalangeal and carpometacarpal joints of the thumb, hip, knee, metatarsophalangeal joint of the big toe and the cervical and lumbar areas of the spine
SECONDARY: This can develop on any joint as a sequel to a joint lesion resulting from intra-articular causes, including rheumatoid arthritis and extra-articular arthritis.

The lesion can be acute, like a fracture, chronic, such as the result of the occupational overuse of a joint, or a metabolic disease (for example, Hyperparathyroidism, hemochromatosis, ochronosis).

Secondarily, obesity constitutes a significant risk factor for the development of osteoarthritis in knees and probably in hips too. The most common symptom of osteoarthritis is pain after the overuse or prolonged inactivity of the joint. This has an insidious start, at the start there is joint stiffness, which seldom lasts for longer than 15 minutes, pain later develops when the affected joint is moved and gets worse with activity, when carrying weight and is relieved by rest. The deformity can be minimum or non-existent. However, the bone growth of the interphalangeal joints is notable and flexion contracture and varus deformity of the knee are frequent. There is no ankylosis, but the limitation of movement in the affected joint or joints is frequent. A rough crepitus can frequently be felt in the affected joint, joint leak and other signs of inflammation are slight.

Ankylosing Spondylitis (AE) is a rheumatic disease that causes inflammation in the joints of the spine and the sacroiliac joints. This usually manifests with phases of lumbar pain that can affect the entire column and peripheral joints and causes pain in the spine and joints, a stiff spine, loss of mobility and progressive joint deformity. This can be accompanied by extra-articular manifestations, such as the inflammation of eyes or heart valves.

It usually appears in adolescence or youth and its incidence is higher in men. Whereas women can present with a milder form of the disease which makes it harder to diagnose. Its incidence also varies in different racial groups.

Night pain and a loss of mobility in the lumbar region are early manifestations. Although, in most cases, the symptoms start in the lumbar and sacroiliac zone, it also usually affects the cervical and dorsal segments of the column.

Back pain is one of the most common causes of medical consultation in general and visits to Pain Units, in particular.

According to estimates, 4% of people suffer lumbar pain every year and more than 70% of the population suffer at least one episode of lumbar pain in their lives.

Lumbalgia is defined as the pain sensation circumscribed to the lumbar spine that impedes its normal mobility. It is called acute lumbalgia if it lasts for less than 3 months and chronic after this temporary limit when accompanied by intolerance to stress, with or without the lower limbs being affected.

In lumbar pain, the mechanical symptoms are more frequent (90%), being unleashed by the movement of the spine and disappearing when the patient is in repose. In contrast, the inflammatory symptoms are continuous, persistent and intense and are not eased with the immobility. Within this, the insidious, constant, intense and maddening pain that increases with immobility and prevents sleep would be characteristic of neoplastic pain.

Gout is a disorder of the metabolization of purines, derivatives of proteins. When there is an overproduction and they accumulate and are not channeled in the proper way, there is an accumulation of uric acid, which can be deposited in a variety of sites except for in the blood, this always derives towards the kidney or the joint, in such a way that nephritis can be caused by uric acid, which evidently conditions urinary stones or urinary crystals, or are derived to the joint, giving rise to what is called gout.

Joint inflammation can become chronic and deforming after repeated attacks. Almost 20% of people affected by gout develop kidney stones.

Bursitis and/or tendinitis is the inflammation of a tendon (insertion of the muscle in the bone) or of a bursa (small sacs that facilitate the movements of the muscle and tendons over the bone). Both structures are next to the joint and therefore their inflammation manifest with symptoms of pain in the joint.

The symptoms are pain and an inability to move the joint located beside the affected tendon or bursa. The area is inflamed and the areas that are most often affected are elbows, shoulders, feet, ankles, knees, hips, wrists and fingers.

The inflammation is owing to: overload of the zone (lesions), therefore when the acute symptoms cede they do not leave any residual lesions.

Psoriatic arthritis (AP) is a disease of the joints that occurs in 10-20% of people who suffer skin psoriasis, which gives it some particular characteristics in terms of its evolution and prognosis. The joint lesion is inflammatory, in other words, with pain, swelling, heat, difficulty of movement of the inflamed joint and the possibility of deformity in the long run.

This is a chronic disease that evolves irregularly throughout the patient's lifetime, with periods of inactivity and periods of inflammation and pain.

The form it appears is different for each individual, there being five established forms:
1. Asymmetric oligoarticular arthritis that affects some of the joints in the limb. This is the most common form.
2. Arthritis that mainly affects the distal interphalangeal joints of the hands.
3. Symmetric arthritis similar to another joint disease called rheumatoid arthritis.
4. Mutilating arthritis, which is very rare, though albeit destructive and deforming.
5. Arthritis that affects the spine and joint of the pelvis or sacroiliac joints in a similar way to another rheumatic disease called ankylosing spondylitis.

Psoriatic arthritis usually starts in people between 30 and 50 years of age but can affect people of any age and sex, including children.

The joint symptoms are common to any type of arthritis: Pain, heat, reddening, inability to move the joint and, sometimes, the deformity thereof. Any joint can be affected, from the joint of the jaw to the joint of the little toe (both very common). If the inflammation happens in the spine, preferably in the joint between the lumbar and the pelvis (the sacroiliac joint), one of the most dominant symptoms is nighttime pain, in the region of the buttocks, that makes the patient get up in the early morning after only 4 or 5 hours of sleep. Pain in the heels is also common when taking the first steps on getting up, as is a sharp pain in the thorax when deep breathing. Another joint symptom is stiffness lasting for more than half an hour when getting up in the morning. It is hard to open and close hands; with the movement, the joint feels as if it is rusty and it is hard to even hold a toothbrush.

It affects approximately 2 to 3% of the world's population: 25 to 34% of these patients have psoriatic arthritis. In over 80% of these patients, the skin disease appears first, and, on average, the symptoms of the psoriasis precede the psoriatic arthritis by 10 years.

The IASP (International Association for the Study of Pain) defines pain as "an unpleasant sensory and emotional experience associated with actual or potential tissue damage, or described in terms of such damage".

Pain is highly prevalent and has a huge impact on the individual, family life, work, society and the economy.

It has been scientifically observed that a high prevalence of excess weight (obesity and overweight) in subjects with knee osteoarthrosis worsens the clinical profile, creating more pain and functional deterioration.

Furthermore, the metabolic syndrome, which is clearly significant as a cardiovascular risk factor, is highly prevalent in some autoimmune rheumatic diseases, according to a variety of studies, as it has been found in 35% of patients with ankylosing spondylitis and 36.2% of patients with primary antiphospholipid syndrome.

Rheumatic diseases, furthermore, are not exclusive to adults. The diseases that can affect young people from early childhood include: juvenile rheumatoid arthritis and juvenile spondyloarthropathies; both can occur at an early age and, if they are not treated on time, can have very severe repercussions such as joint deformities, functional disability and different degrees of invalidity with deterioration in the quality of life and their performance in society that continue into adulthood.

It is worth mentioning that rheumatic diseases in general are more common than other pathologies that are better known by the general public. When pain is the main initial symptom, it is possible and highly probable that the affected patient will resort to self-medication with painkillers, nonsteroidal anti-inflammatory drugs or common steroids, before seeking specialist medical attention. There will be complications if the GP does not make the right diagnosis or does not refer the patient to the right specialist. Any delay in starting treatment probably adversely affects the patient's functional prognosis consequently generate high rates of temporary disability and invalidity; high costs for medical attention; high costs of lost productivity; deterioration in quality of life and, in the worst case, the death of the patient prematurely.

In the face of the above dilemma, the strategy of combining existing products that are effective as monodrugs is successful as it permits their mechanisms of action to complement each other, in order to improve their clinical safety and obtain a better therapeutic benefit.

It has been proven that these drugs applied topically achieve sufficient concentrations on the skin and in the underlying tissue for a total or partial reduction in the pain of rheumatic disease.

The groups of active ingredients for the control or treatment of rheumatic diseases include nonsteroidal anti-inflammatory drugs, which are one of the most prescribed groups of drugs in the world. NSAIDs are useful for rheumatic pain, in both inflammatory and degenerative diseases and are also often used for non-rheumatic diseases such as for migraines, toothache and, in general, for any pain process because of its painkilling effect. Moreover, these active ingredients are useful as antipyretics. It is worth mentioning that in recent years these NSAIDs has been shown to have an effect in protecting against colon cancer. Their use by the general public is widespread, including as self-medication, given that they can often be obtained without any need for a prescription or medical control, with the risk of potential side effects.

The nonsteroidal anti-inflammatory drugs include the following active ingredients: acetylsalicylic acid, salsalate, diflunisal, fosfosal, acetyllysine, phenylbutazone, indometacin, tolmetin, sulindac, acemetacin, diclofenac, aceclofenac, nabumetone, ibuprofen, naproxen, ketoprofen, flurbiprofen, piroxicam, tenoxicam, meloxicam, mefenamic acid, meclofenamate, celecoxib, etoricoxib and lumiracoxib.

Out of the above active ingredients, aceclofenac possesses painkiller and antipyretic properties. At experimental level, it inhibits the formation of edema and erythema, irrespective of the etiology of the inflammation. The study of its mechanisms of action, in both animals and humans, shows that aceclofenac inhibits the formation of prostaglandins and leukotrienes through the reversible inhibition of cyclooxygenase.

The chemical name of aceclofenac is: (2-{2-[(2,6-Dichlorophenyl)amino]phenyl}acetoxy) acetic acid; and is represented by the following molecule (1):

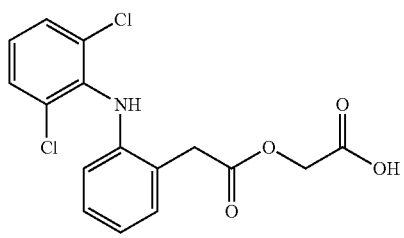 [SMILES: O=C(O)COC(=O)Cc1ccccc1Nc1c(Cl)cccc1Cl]

Described for the first time in the United States patent U.S. Pat. No. 4,548,952 which has anti-inflammatory and aesthetic properties.

When applied to the skin, aceclofenac is rapidly absorbed. The amount of aceclofenac absorbed is 13% of the total dose applied; likewise, the amount of aceclofenac that is retained on the top layers of skin is from 6 to 9% of the dose applied, which concentration slowly declines over more than 16 hours, after the drug product is removed from the skin, for it to then get into the general circulation.

The other group of anti-inflammatory active ingredients are corticosteroids, that also have immunosuppressant properties. Corticoids are a group of active ingredients that have been massively used for a long time now by a wide range of specialists, as they are highly effective and produce good known benefits in numerous clinical situations. However, it is worth pointing out that a lot of the uses of corticoids are empirical, without their mechanism of action, effective dose or their clinical effectiveness having been studied. The group of corticosteroids includes the active ingredients: Hydrocortisone or cortisol, cortisone, prednisone, methylprednisolone, deflazacort, fludrocortisone, triamcinolone, paramethasone, betamethasone and dexamethasone.

Corticoids can be administered in different pathways. It is important to know the advantages and limitation of each of them. The wrong choose of pathway tends to entail a higher rate of iatrogenism, higher costs and less therapeutic effectiveness. Sometimes it may be desirable to apply the corticoids locally whereas, in other circumstances, a systemic effect may be sought.

Topical corticoids have been used for inflammatory diseases since the 1950s. This is because they have a series of advantages without many side effects.

Among the many advantages, it is worth mentioning: a) their utility in multiple inflammatory processes, their speed of action; their ease of application, and their stability in the vehicle.

They have a common skeletal structure, the cyclopentanoperhydrophenanthrene core, with 17 carbon atoms arranged in 4 rings. Certain modifications increase their potency: double bonds in C1-C2, halogenization in C6, C9, the addition of hydroxyl groups or carbon chains such as acetonides, valerates and propionates.

Modifications of these primary structures enable the production of compounds of varied potency and toxicity.

Their mechanism of action is intracellular: once in the cytoplasm, there are some specific intracytoplasmic receptors, in which these drugs are transported to the core, where they join the region of the "corticoid response element", which inhibits or stimulates the adjacent gene transcription and regulates the inflammatory process.

To obtain topical utility, suitable concentrations must be achieved on the epidermis without reaching a high serum level. After their application they create a skin reservoir, so it is not necessary, in theory, to apply them more than once a day or even more than once every two days.

The anti-inflammatory potency of a topical corticoid is measured by its ability to produce cutaneous vasoconstriction and is used to make a scale in proportion to its relative potency (Stoughton test). So, its effectiveness is in relation to potency, as are its side effects. In general, fluoro derivatives (betamethasone, fluocinolone, etc.) are more potent than non-fluoro derivatives.

The chemical name of betamethasone is: (11ß,16ß)-9-fluoro-11,17,21-trihydroxy-16-methylpregna-1,4-diene-3,20-dione and is represented by the following molecule (11):

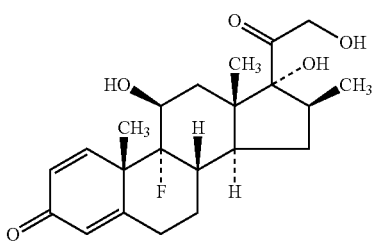

Described for the first time in the United States patent U.S. Pat. No. 3,053,865 describing its anti-inflammatory properties and especially effective for the treatment of arthritis. It is also more specifically described in the United States patent U.S. Pat. No. 3,104,246 together with its preparation process.

Betamethasone reduces inflammation by inhibiting the release of hydrolases from the leukocytes, thus avoiding the accumulation of macrophages in the place where the inflammation is. The administration of betamethasone interferes with leukocyte adhesion to the walls of the capillary vessels, and lowers the permeability of the membrane of the capillary vessels, that causes a reduction of edema. Moreover, betamethasone lowers the release of molecules that promote inflammation, such as histamine and quinines (IL-1, IL-6, TFN-alpha) and interferes with the formation of fibrous tissue.

The anti-inflammatory effects of corticoids are, in general, due to the effects on the lipocortins, proteins that inhibit phospholipase A2. Lipocortins control the synthesis of potent inflammatory mediators such as leukotrienes, prostaglandins, as they inhibit the synthesis of their precursor, arachidonic acid:

9-fluoro-11,17-dihydroxy-17-(2-hydroxyacetyl)-10,13, 16-trimethyl-6,7,8,9,10,11,12,13,14, 15, 16, 17 dodecahydro cyclopenta[a]phenanthrene-3-Betamethasone is a compound with potent glucocorticoid activity and, in contrast, low mineralocorticoid activity; 0.75 mg of betamethasone is equivalent in anti-inflammatory activity to 5 mg of prednisolone. It is 17, 21-dipropionate ester of betamethasone.

Betamethasone is an off-white powder-odorless crystal that is insoluble in water, is quickly absorbed in the gastrointestinal tract, but is also absorbed by skin, is distributed to all the tissues of the body, it binds with the plasma proteins more than with globulin, has a prolonged half-life of 72 hours with an equivalent dose of 0.75 mg; is metabolized in the liver and kidneys and excreted in the urine. The effects of betamethasone on the sodium and water are less than with prednisolone or prednisone.

To cover an anti-inflammatory problem, an effective treatment is required that provides the necessary effect for said problem, with a lower dose than is commonly used, in a shorter time and with fewer adverse effects. Which is why this invention includes the combination of aceclofenac and betamethasone for the treatment of pain in the localized forms of rheumatic complaint.

In the state of the art, the patents U.S. Pat. Nos. 7,070,765 and 7,078,019 describe an aerosol and method of administration through inhalation of ester compounds such as aceclofenac, betamethasone, among other listed compounds, characterized by the fact that the compound has less than 10% of degradation products in weight, and a mean aerodynamic diameter of a mass of less than 5 micrometers; the patent U.S. Pat. No. 8,361,492 describes a drug administration system that comprises: a contact lens of electrospun fibers incorporated into a polymer lens; wherein the electrospun fibers are prepared by electrospinning a polymer solution into a mat of fibers, applying a cross-linking treatment to the mat of fibers, and applying a polymer coating to the mat of fibers; and at least one therapeutic drug chosen from aceclofenac or betamethasone or other compounds; the U.S. Pat. No. 9,597,527 patent describes a dermal system in the form of a transdermal patch that comprises at least one light source that issues infrared irradiation with a maximum emission of 700 nm at 3 mm selected from organic light emitting diodes, polymeric light emitting diodes and at least one pharmaceutical and/or cosmetically active ingredient chosen from aceclofenac and betamethasone for the treatment and/or prophylaxis of acute and chronic pain, muscular pain, joint stiffness, muscular tension and stiffness, mood disorders, menopause, osteoporosis, angina, acute injuries, arthritis, nicotine addiction, viral infections, inflammation, tumors and cancer; patent MX 348595 refers to a solid three-phase delayed-release and/or controlled release and/or modified release and/or fast release system, of at least three layers for the formation of at least one dosing unit, where each layer includes as active pharmaceutical ingredients at least one corticosteroid agent like betamethasone and/or its pharmaceutically acceptable salts, at least a nonsteroidal anti-inflammatory agent like aceclofenac and/or its pharmaceutically acceptable salts, at least one excipient that is pharmaceutically acceptable for the treatment of inflammation and bodily pain.

This invention is characterized by providing a composition that comprises the combination of aceclofenac with betamethasone in the semi-solid form or as a solution not reported in the state of the art. The potential advantage of using the therapy of said combination is that the analgesic effects can be maximized, while the incidence of adverse effects is minimized.

The use of this combination of drugs offers an analgesic synergy that permits a reduction in the necessary doses together with a reduction in the adverse effects.

OBJECT OF THE INVENTION

To offer a new therapeutic option for the control and treatment of rheumatic pain that manages to reduce the patients' symptomatology and improve their quality of life. This is done by applying the strategy of combining aceclofenac or its pharmaceutically acceptable salts with betamethasone or its pharmaceutically acceptable phosphate or dipropionate salts, which generates a synergic interaction, increasing their therapeutic potency, onset of action and reduction of adverse events.

Said combination improves the therapy, offering benefits such as: the application of smaller concentrations of the active ingredients than those used when administered separately; better effectiveness and greater therapeutic potency in the time of its application, aimed at achieving localized therapeutic effects for the treatment and control of pain in rheumatic conditions; apart from significantly lowering the probability of side effects.

DETAILED DESCRIPTION OF THE INVENTION

Figure 1:
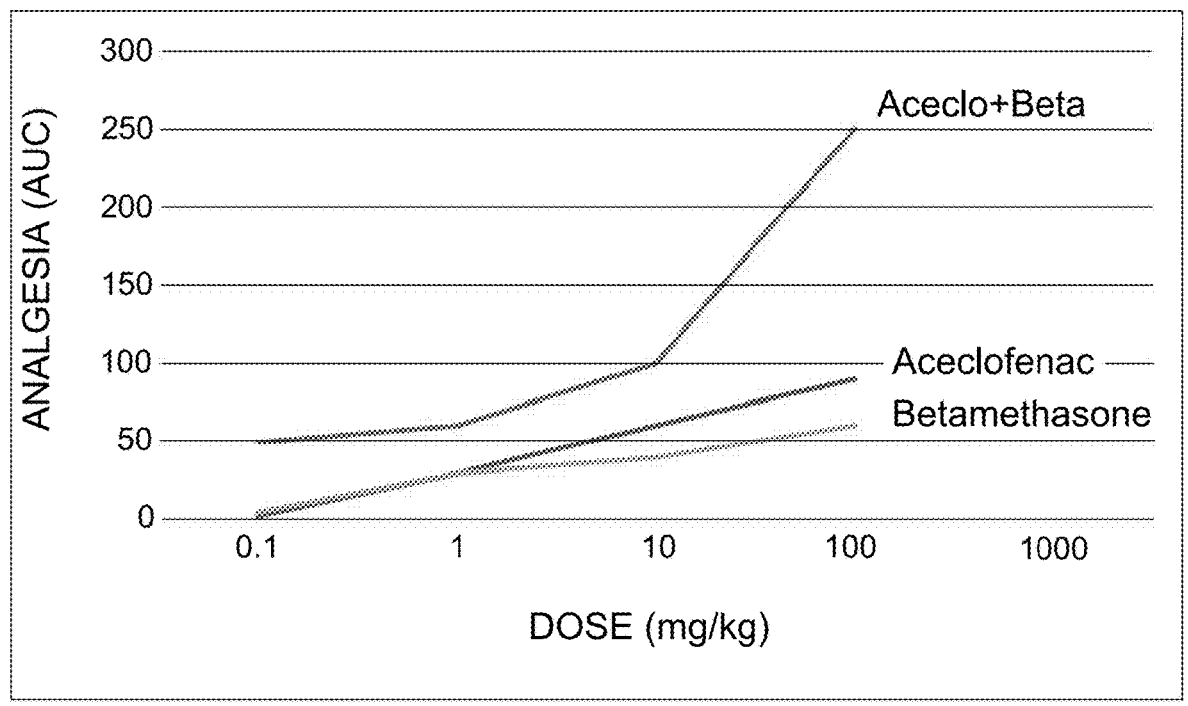
FIG. 1. Dose-Response Curve for each compound in topical administration (Model PIFIR AU 20%).

This invention refers to the novel pharmaceutical composition for topical administration, containing at least one nonsteroidal anti-inflammatory agent, such as aceclofenac or its pharmaceutically acceptable salts, and at least one corticosteroid agent, such as betamethasone or its pharmaceutically acceptable phosphate or dipropionate salts, where said active pharmaceutical ingredients provide synergic effects at the moment of their application to achieve localized therapeutic effects for the treatment and control of pain in rheumatic conditions The synergic formulation of aceclofenac+betamethasone for topical application seeks to avoid the systemic absorption as much as possible, and provide a local, fast and effective analgesic and anti-inflammatory effect.

The proposal is that the combination, in the pharmaceutical form of semi-solid or solution, of aerosol of aceclofenac+betamethasone is an effective therapeutic resource in patients with the localized forms of pain of rheumatic conditions, with a profile of minimum or inexistent adverse events, and a significant local analgesic and anti-inflammatory action. The concomitant use of glucocorticoids as is the case of betamethasone together with a nonsteroidal anti-inflammatory drugs (aceclofenac) provides an additive therapeutic effect that makes it possible to achieve a significant favorable impact at population level.

This invention has proven by means of trial studies on a preclinical model that the novel combination of aceclofenac and betamethasone for topical administration or application has an unexpected and strong synergic therapeutic effect in the treatment of local rheumatic pain; so the main aim of this invention is the development of a pharmaceutical composition consisting of the combination of a nonsteroidal anti-inflammatory agent, such as aceclofenac, and a corticosteroid agent, such as betamethasone or its pharmaceutically acceptable salts, as phosphate and dipropionate. Said combination is formulated with pharmaceutically acceptable excipients and is indicated for the control and treatment of local rheumatic pain.

One currently available alternative for increasing the effectiveness of an analgesic treatment and significantly lowering the side effects is through the administration in combination of two or more active agents, such as the synergistic drug combination whose protection is being sought in this invention.

This invention seeks to provide a new therapeutic option for the control and treatment of rheumatic pain, that manages to reduce the patients' symptomatology and improve their quality of life.

At the present time the effects that the topical form of the combination of aceclofenac and betamethasone (long-lasting, potent anti-inflammatory steroid) can produce have not been determined, however, this combination seems to have adequate usefulness and effectiveness. For which purpose, this paper determined and assessed the analgesic effect after topical application in animals with gout in comparison to the effects produced by the individual topical administration of aceclofenac and betamethasone.

Method

Animals for Experimentation

Female Wistar rats [Crl:(WI)BR] were employed with a weight of between 180 and 200 g. All the experimental procedures followed the recommendations of the committee for Research and Ethical Issues of the International Association for the Study of Pain and the Guidelines on Ethical Standards for Investigations of Experiment Pain in Animals. The number of animals for experimentation was kept to a minimum: 6 rats per experimental point. The animals were kept in a room with alternating dark/light cycles.

Twelve hours before the experiments, the fur that covers the rats' major muscle group that covers the femur (4 cm×4 cm) on the outer side of the hind right paw was very carefully clipped with some scissors, leaving the fur cut to a maximum length of 2 mm and taking care not to injure the rats' skin. Food was also removed at this moment, leaving them only free access to water. All the experiments were performed during the light phase, with the animals only being used once.

Experimental Model

Assessment of the Analgesic Activity

The analgesic effects are assessed employing the PIFIR model, in other words, the rats were anesthetized in a glass desiccator, saturated with ether vapor. The gout was induced by applying an intra-articular injection (i.a.) of 0.05 ml of uric acid suspended in mineral oil in the right hind member, exactly in the femur-tibia-kneecap joint. A 1 mL glass syringe with a 4-mm-long No. 22 needle is used for the intra-articular injection. Immediately afterwards, an electrode is attached to each hind paw in the middle of the plantar calluses. The rats were left to recover from the anesthesia and placed in a 30-cm-diameter rotary stainless-steel cylinder. The cylinder was turned at 4 r.p.m., forcing the rats to walk for 3 min every half hour, for a total of 5 hours. The variable measured was the contact time of each one of the rats' hind paws in the cylinder. When the electrode makes contact with the cylinder a circuit is closed and the ratio between the contact time of the injured paw in respect of the uninjured one was recorded on a computer.

Experimental Protocol

The analgesic effects produced by aceclofenac-betametasone, aceclofenac by itself, betamethasone by itself and pharmaceutically acceptable vehicles and/or excipients were individually studied making the topical application exactly 1 h after the administration of the uric acid at 20% and assessing the functionality every 0.5 hours for the following 6 hours. The doses that were assessed for each of the compounds were as follows: aceclofenac-betametasone (3.2, 5.6, 10, 17.8 and 31.6 mg/Kg by topical administration), aceclofenac (3.2, 5.6, 10, 17.8 and 31.6 mg/Kg by topical administration), betamethasone (3.2, 5.6, 10, 17.8 and 31.6 mg/Kg by topical administration), and pharmaceutically acceptable excipient and/or vehicle 10 and 31.6 mg/Kg by topical administration. Simultaneously the effects that cutting their fur had on the functionality of the rats, following the complete experimental protocol, but without applying the treatment topically, were also determined as a control.

The temporary courses of each treatment for 5 continuous hours were determined, employing an "n" of 6 rats per treatment. For the purpose of this study, inducing harm in the experimental animals was unavoidable. However, care was taken to avoid causing unnecessary suffering to the animals. At the end of the experimental determinations, the rats were immediately sacrificed.

From the aforementioned experimental model, the results obtained from the analgesic assessment of the combination are expressed as a Functionality Index percentage (FI %). This FI % is the ratio obtained by dividing the contact time of the limb with uric acid by the contact time of the limb against of the same rats, and multiplying the result by 100. The temporary course (TC) curves are built by plotting FI % or Dysfunction against time (h). The analgesic or antinociceptive effect was estimated as the recuperation of FI %. The analgesic effect accumulated during the total observation period (5 h) was determined to be the area under the curve (AUC) of the TC, according to the trapezoidal rule. All the values plotted in the figures correspond to the mean±error standard for 6 animals.

The uric acid at 20% induced a complete disfunction of the right hind leg approximately 2.5 h after administration, this corresponded to a value of zero for the FI %. The rats that only received the uric acid at 20% or the vehicle in 10 mg/Kg and 31.6 mg/Kg doses by topical administration did not show any significant recovery of the FI % during the observation period of 5 h. The doses of aceclofenac-betametasone, aceclofenac or betamethasone that were used did not affect the ability of the rats to walk during the observation period or cause any visible adverse effect.

Regarding the temporary courses (TC) developed for topical betamethasone in 3.16, 10.0 and 17.8 mg/Kg doses for topical administration, we observed that betamethasone does not generate analgesic effects at those doses. Furthermore, the TC developed by betamethasone in doses of 31.6 mg/Kg for topical administration generated modest analgesic effects, particularly at the end of the assessment period (5 hours). In this presentation and assessment plan, the maximum effect appeared at the 3.5 h point (13.1±4.7%).

After the analysis of betamethasone, the TC for aceclofenac in 3.16, 5.62, 10.0, 17.78 and 31.62 mg/Kg doses given by topical administration was also obtained. The Aceclofenac in the administered dose does show analgesic effects and, consequently, also adequate absorption to generate analgesic effects. The analgesic effects presented had a slow onset of action but gradually growing over time, in such a way that 5 hours after having been administered, the analgesic effects can still be noted under these experimental conditions. The Emax value with the 31.6 mg/Kg dose was 42.0±6.9% at precisely the end of the assessment period.

Regarding the application of the combination of aceclofenac and betamethasone, the TCs are presented for the analgesic effects developed by the administration of said compounds in semi-solid form in 3.16, 5.62, 10.0, 17.78 and 31.62 mg/Kg doses by topical administration. A significant dose-dependent increase was produced in the analgesic effects. Even when there is a slow onset of action, the analgesic effect grows significantly after the point marked as 2.0 hours reaching practically 79.7±8.3 units of area of analgesia at the end of the assessment period after the administration of the 31.6 mg/Kg dose. We observe that the effect seems continue for much longer than 5 hours, which cannot be monitored owing to the limitations that the experimental model has after the 5 hours of assessment.

Derived from the above results the dose-response curve (DRC) was implemented, as shown in FIG. 1, in which, based on said behavior, we can corroborate that the combination gives better analgesia in comparison to the analgesia provided by the independent application of each compound.

Figure 2:
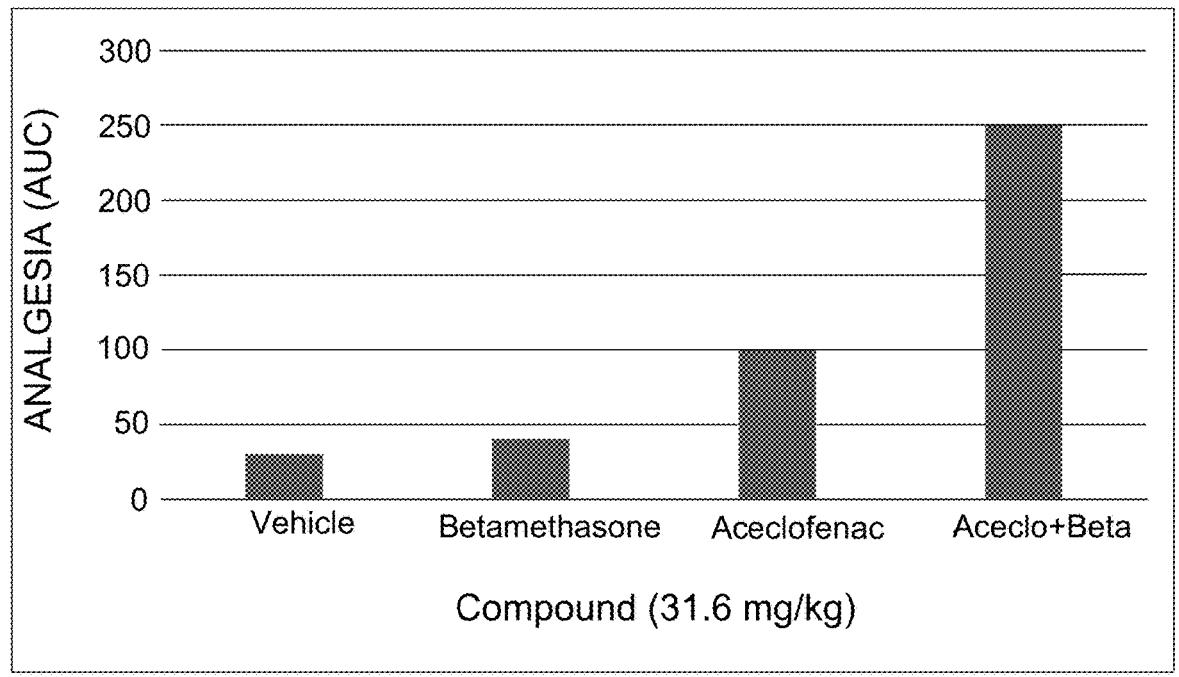
FIG. 2. Area under the curve for the highest dose of every compound analyzed through topical (Model PIFIR AU 20%).

Likewise, FIG. 2, that represents the maximum effect, shows through the area under the curve (AUC) for the highest dose of 31.6 mg/kg, produced by each of the compounds and the combination administered topically. It is very clear that the administration of aceclofenac in combination with betamethasone in semi-solid form generates much more analgesic effects and significantly improves analgesic effectiveness. The overall analgesic effect is assessed and found to be much better with said combination.

The data obtained confirm the evidence of pharmacological—in this case, analgesic—effects and that the compounds can be properly absorbed as well as, on the other hand, that the association of aceclofenac compounds with betamethasone compounds continues to prove that there is adequate and high analgesic activity in comparison to when these components are administered individually.

These results confirm that there is a very good interaction between the aceclofenac+betamethasone components that produce a significant improvement in their analgesic effectiveness. All the treatments were administered simultaneously and assessed in the same way, in order to avoid variations caused by handling, the weather or the environment.

In the current state of the art, there are pharmacological treatments for pain, however, there is no one treatment that is characterized by the combination of the active agents, aceclofenac, or its pharmaceutically acceptable salts, with betamethasone, or its pharmaceutically acceptable phosphate or dipropionate salts, in the topical administration form, which is why the development of this invention provides a real and safe alternative for the control and treatment of rheumatic pain, managing to lower treatment times, therapeutic effects and secondary reactions. The administration of said compounds is given in an amount of approximately 0.01 mg to approximately 10,000 mg of treatment for aceclofenac per 100 g of formula, whereas, for betamethasone, it is given in an amount of approximately 0.001 mg to approximately 10,000 mg per 100 g of formula.

This invention has been developed for topical and transdermal administration, either in a semi-solid pharmaceutical form such as a cream, ointment or gel; pharmaceutical form such as a solution for aerosol; pharmaceutical form such as an transdermal patch; in the form of an intramuscular or intravenous injectable; either in the form of fast release for both drugs or modified release for one or both drugs, with a smaller dose, there is greater therapeutic potency and a lower risk of adverse events.

EXAMPLES

A description is given below, by way of illustration and not as a limitation, of some pharmaceutical compositions:

Example 1: Compositions for Topical and Transdermal Administration

Aceclofenac
Betamethasone or its pharmaceutically acceptable phosphate or dipropionate salts
Pharmaceutically acceptable excipient and/or vehicle Example 2: Composition for Intramuscular and Intravenous Administration Aceclofenac
Betamethasone or its pharmaceutically acceptable phosphate or dipropionate salts
Pharmaceutically acceptable excipient and/or vehicle This invention can be represented in other specific forms without losing its spirit or essential characteristics. The modes described shall, in all their aspects, be treated only as examples and not as restrictions. Therefore, the scope of this invention is given in the attached claims rather than in the above description. Its scope shall include all the changes that fall within the meaning and range of equivalence of the claims.

Overall, this invention has the following advantages:
1. In respect of the absorption of the formulations, its proper absorption could be proven by the evidence of analgesic effects under the established experimental conditions.
2. In respect of the effectiveness, aceclofenac with betamethasone showed more analgesic effectiveness than that obtained for the aceclofenac or betamethasone compounds when they are administered independently, using the gout experimental model.
3. In respect of the onset of action: aceclofenac with betamethasone and aceclofenac have a very similar onset of action.
4. In respect of the length of time of the analgesic effect: the analgesic effects were analyzed for 5 continuous hours, and those effects were very good up to and including that hour, both for aceclofenac combined with betamethasone and for aceclofenac by itself.
5. In respect of Emax: aceclofenac with betamethasone showed the highest Emax in TC.
6. In respect of overall analgesic effectiveness (AUC) assessed over 5 continuous hours: aceclofenac combined with betamethasone had a better effect than the effect obtained from the simple administration of each compound.

The invention claimed is:
1. A pharmaceutical composition consisting of a synergic combination of:
   i. aceclofenac in basic form,
   ii. betamethasone in a phosphate or a dipropionate salt, and
   iii. a pharmaceutically acceptable vehicle and/or excipient,
   wherein the aceclofenac in basic form is present in the composition in an amount that is 15 times greater than the amount of the betamethasone in phosphate or dipropionate salt;
   wherein the composition is formulated as a topical gel or cream.
2. A method of treating rheumatic pain in a human comprising administering to the human and effective amount of a pharmaceutical composition, thereby treating the rhematic pain;
   The pharmaceutical composition consisting of a synergic combination of:
   i) aceclofenac in basic form;
   ii) a phosphate or a dipropionate salt of betamethasone; and
   iii) a pharmaceutically acceptable vehicle and/or excipient,
   wherein the aceclofenac in basic form is present in the composition in an amount that is 15 times greater than the amount of the betamethasone in phosphate or dipropionate salt; wherein the composition is formulated as a topical gel or cream.

* * * * *

UNITED STATES PATENT AND TRADEMARK OFFICE
CERTIFICATE OF CORRECTION

PATENT NO. : 12,290,526 B2
APPLICATION NO. : 17/267239
DATED : May 6, 2025
INVENTOR(S) : Patricia del Carmen Garcia Armenta It is certified that error appears in the above-identified patent and that said Letters Patent is hereby corrected as shown below:

On the Title Page

Item (30), "A/2018/009812" should be -- MX/A/2018/009812 -- therefor.

In the Claims

In Claim 2, at Column 14, Line 15, delete "and effective amount" and insert -- an effective amount -- therefor.

In Claim 2, at Column 14, Lines 16-17, delete "rhematic pain;" and insert -- rheumatic pain; -- therefor.

In Claim 2, at Column 14, Line 18, delete "The" and insert -- the -- therefor.

Signed and Sealed this
Tenth Day of June, 2025

Coke Morgan Stewart
*Acting Director of the United States Patent and Trademark Office*